United States Patent
Bellman et al.

(10) Patent No.: US 7,218,802 B1
(45) Date of Patent: May 15, 2007

(54) LOW DRIFT PLANAR WAVEGUIDE GRATING SENSOR AND METHOD FOR MANUFACTURING SAME

(75) Inventors: Robert A. Bellman, Painted Post, NY (US); Chuan-che Wang, Ithaca, NY (US)

(73) Assignee: Corning Incorporated, Corning, NY (US)

( * ) Notice: Subject to any disclaimer, the term of this patent is extended or adjusted under 35 U.S.C. 154(b) by 10 days.

(21) Appl. No.: 11/292,400

(22) Filed: Nov. 30, 2005

(51) Int. Cl.
G02B 6/00 (2006.01)
G02B 6/34 (2006.01)
G02B 6/10 (2006.01)

(52) U.S. Cl. ............... 385/12; 385/37; 385/130; 385/131

(58) Field of Classification Search ............ 385/12, 385/14, 37, 129, 130, 131, 141
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 5,071,248 A | 12/1991 | Tiefenthaler et al. | 356/128 |
| 5,262,842 A | 11/1993 | Gauglitz et al. | 356/345 |
| 5,369,722 A | 11/1994 | Heming et al. | 385/130 |
| 5,415,842 A | 5/1995 | Maule | 422/82.05 |
| 5,455,178 A | 10/1995 | Fattinger | 436/164 |
| 5,480,687 A | 1/1996 | Heming et al. | 427/573 |
| 6,218,194 B1 | 4/2001 | Lyndin et al. | 436/518 |
| 6,320,991 B1 | 11/2001 | Challener et al. | 385/12 |
| 6,332,363 B1 | 12/2001 | Molloy et al. | 73/776 |
| 6,429,022 B1 | 8/2002 | Kunz et al. | 436/164 |
| 6,470,130 B1 * | 10/2002 | Walker et al. | 385/142 |
| 6,483,959 B1 | 11/2002 | Singh et al. | 385/12 |
| 6,493,090 B1 | 12/2002 | Lading et al. | 356/484 |
| 6,804,445 B2 | 10/2004 | Edlinger et al. | 385/131 |
| 6,873,764 B2 | 3/2005 | Maisenholder et al. | 385/37 |
| 6,915,029 B2 * | 7/2005 | Lee et al. | 385/14 |

(Continued)

FOREIGN PATENT DOCUMENTS

| | | | |
|---|---|---|---|
| WO | WO 88/10418 | 12/1988 | 436/527 |

(Continued)

OTHER PUBLICATIONS

J. Liu et al., "Etch Rate And Surface Morphology of Plasma Etched Glass and Glass-Ceramic Substrates", Journal of Non-Crystalline Solids, vol. 342, 2004, pp. 110-115, no month available.
S.E. Kim et al., "Metal/Fluorinated-Dielectric Interactions In Microelectronic Interconnections: Rapid Diffusion of Fluorine Through Aluminum", Applied Physics Letters, vol. 75, No. 13, Sep. 27, 1999, pp. 1902-1904.
D.L. Smith, "Thin Film Deposition: Principles and Practice", McGraw-Hill, 1995, pp. 159-161, no month available.
D.L. Smith, "Thin Film Deposition: Principles and Practice", McGraw-Hill, 1995, pp. 119-180, no month available.

(Continued)

*Primary Examiner*—Quyen Leung
(74) *Attorney, Agent, or Firm*—William J. Tucker, Esq.; Thomas R. Beall

(57) ABSTRACT

A planar waveguide grating (PWG) sensor is described herein which exhibits a low signal drift and an enhanced sensitivity due to the use of a fully dense silicon-rich nitride surface layer. In the preferred embodiment, the silicon rich silicon nitride surface layer has a composition which includes Si and N, and optionally H, Ge and/or O, where a Si/N atomic ratio is greater than 0.75. In addition, the silicon rich nitride surface layer has a refractive index that is greater than 2.45 and less than 3.2 at a wavelength of operation. A method is also described herein for manufacturing the PWG sensor with acceptable costs and high yields by utilizing well known semiconductor processes and tools.

23 Claims, 13 Drawing Sheets

U.S. PATENT DOCUMENTS

| | | |
|---|---|---|
| 2003/0017580 A1 | 1/2003 | Cunningham et al. ... 435/287.2 |
| 2003/0017581 A1 | 1/2003 | Li et al. .................. 435/287.2 |
| 2003/0027328 A1 | 2/2003 | Cunningham et al. ... 435/287.2 |
| 2004/0043508 A1 | 3/2004 | Frutos et al. ............... 436/518 |
| 2004/0087135 A1 | 5/2004 | Canaperi et al. ............ 438/628 |
| 2005/0025421 A1 | 2/2005 | Caracci et al. ................ 385/37 |

FOREIGN PATENT DOCUMENTS

| | | |
|---|---|---|
| WO | WO 98/09156 | 3/1998 |
| WO | WO 00/20848 | 4/2000 |
| WO | WO 02/35214 | 5/2002 |
| WO | WO 02/082130 | 10/2002 |

OTHER PUBLICATIONS

D.L. Smith, "Thin Film Deposition: Principles and Practice", McGraw-Hill, 1995, pp. 442-446, no month available.

M. Ohring, "The Materials Science of Thin Films", Academic Press, Boston, 1992, pp. 181-183, no month available.

W.R. Knolle, "Correlation of Refractive Index and Silicon Content of Silicon Oxynitride Films", Thin Solid Films, vol. 168, 1989, pp. 123-132, no month available.

H. Yang et al., "Stability of Si-O-F Low-K Dielectrics: Attack By Water Molecules as Function of Near-Neighbor Si-F Bonding Arrangements", J. Vac. Sci. Technol. A, vol. 16, No. 3, May/Jun. 1998, pp. 1525-1528.

* cited by examiner

LOW DRIFT PLANAR WAVEGUIDE GRATING SENSOR AND METHOD FOR MANUFACTURING SAME

BACKGROUND OF THE INVENTION

1. Field of the Invention

The present invention relates to a planar waveguide grating (PWG) sensor which exhibits a low signal drift and an enhanced sensitivity due to the use of a fully dense silicon rich silicon nitride surface layer. In addition, the present invention relates to a method for manufacturing the PWG sensor with acceptable costs and high yields by utilizing well known semiconductor processes and tools.

2. Description of Related Art

The following abbreviations are herewith defined, at least some of which are referred to in the ensuing description of the prior art and the preferred embodiments of the present invention.

| | |
|---|---|
| APCVD | Atmospheric Pressure Chemical Vapor Deposition |
| CVD | Chemical Vapor Deposition |
| FIB | Focused Ion Beam |
| FSG | Fluorine Doped Silica Glass |
| LPCVD | Low Pressure Chemical Vapor Deposition |
| PECVD | Plasma Enhanced Chemical Vapor Deposition |
| PWG | Planar Waveguide Grating |
| PVD | Physical Vapor Deposition |
| RIE | Reactive Ion Etching |
| SACVD | Sub-Atmospheric Chemical Vapor Deposition |
| SEM | Scanning Electron Microscopy |
| SPR | Surface Plasmon Resonance |
| UV | Ultraviolet |

Evanescent field-based sensors are fast becoming a technology of choice for accurate label-free detection of a biological, biochemical, or chemical substance (e.g., cells, spores, biological or drug molecules, or chemical compounds). The label-free detection technology typically involves using a PWG sensor or a SPR sensor to detect a change in the refractive index of liquid or gas immediately above the sensor. For example, the change in refractive index can arise from a concentration change, surface adsorption, reaction, or the mere presence of a biological or chemical substance at the sensor's surface. Several types of known PWG sensors are described next each of which have different structures and materials of construction. And, then a description is provided about what causes a problematical signal drift which adversely affects the sensitivity of those PWG sensors. The cause of this problematical signal drift is addressed by the present invention.

In general, the PWG sensor is made from a substrate, a monomode waveguide and a sub-wavelength period diffraction grating that is formed into either the substrate or the waveguide. FIG. 1 (PRIOR ART) is a diagram which is used to help describe the basic elements and the basic functionality of one type of PWG sensor 100. As shown, the PWG sensor 100 has the following elements:

Substrate 102 (patterned with a sub-wavelength period diffraction grating 104).
Waveguide 106.
Chemically responsive surface chemistry layer 108.
Chemically bound molecules 110 (targets 110) of interest.
Solution 112 containing the substance 114 (analyte 114) to be detected.

Typically, the thickness and refractive index of the waveguide 106 along with the characteristics (pitch, depth, and duty cycle) of the diffraction grating 104 are chosen to yield the highest possible sensitivity to a refractive index change which is caused by the interaction of the analyte 114 and target 110. This sensitivity is defined as the shift in the reflected light 116 relative to the refractive index change (nm/refractive index unit). Because, the sensing principle involves the interaction of an evanescent wave emerging from the waveguide 106, the sensed volume is typically limited to the first 150–200 nm above the surface of the waveguide 106. A more detailed discussion about the structure and the functionality of this PWG sensor 100 can be found in U.S. Pat. No. 4,815,843. The contents of this patent are incorporated by reference herein.

In the past, a lot of work has been done to enhance the performance of the PWG sensor 100. For example, it has been shown that the performance of the PWG sensor 100 can be enhanced by: (1) raising the index contrast between the substrate 102 and the waveguide 106 (see U.S. Patent Application 2005/0025421 and PCT Patent Application WO0235214); (2) producing a highly uniform diffraction grating 104 (see U.S. Pat. No. 6,873,764 B2); (3) lowering unfavorable interactions between the solution 112 containing the analyte 114 (molecules 114) of interest and the waveguide 106 which can result in resonant drift and other detrimental effects (see U.S. Pat. No. 6,332,363); and (4) increasing the amount of analyte 114 binding to the target 110 (receptor 110) by improving the surface chemistry layer 108 or its application (see U.S. Patent Application No. 2004/0043508A1).

In addition, a lot of work has been done in the past to make a disposable PWG sensor 100 so that one does not have to re-use the sensor 100 after performing an assay. This is desirable because if one re-uses the PWG sensor 100 then there is a possibility of cross-contamination. However, there are problems associated with manufacturing disposable PWG sensors 100 at a high yield and a low cost. And, there are problems associated with the performance of these disposable PWG sensors 100. These problems are described next.

The prior art demonstrates that there has been a struggle to balance the cost and performance in making a disposable PWG sensor 100. For instance, the PWG sensor 100 can have a low cost polymeric substrate 102 within which the sub-wavelength gratings 104 can be easily embossed or molded. However, the PWG sensor 100 which has a polymeric substrate 102 can suffer from a problematical optical signal loss that is due to absorption in the polymeric substrate 102. To address this absorption problem, the PWG sensor 100 can be enhanced by depositing a thick oxide or organic modified oxide layer between the polymeric substrate 102 and the waveguide 106. This type of PWG sensor 200 is illustrated in FIG. 2 (PRIOR ART). As shown, the PWG sensor 200 has the following elements:

Polymeric substrate 202 (patterned with a sub-wavelength period diffraction grating 204).
Inorganic cladding layer 205.
Waveguide 206.
Chemically responsive surface chemistry layer 208.
Chemically bound molecules 210 (targets 210) of interest.
Solution 212 containing the substance 214 (analyte 214) to be detected.

For a more detailed discussion about the structure and the functionality of PWG sensor 200, reference is made to the following documents:

U.S. Pat. No. 5,369,722.
U.S. Pat. No. 6,804,445 B2.

The contents of these documents are incorporated by reference herein.

Referring back to FIG. 1, it can be difficult to manufacture the PWG sensor 100 which has a polymeric substrate 102. In particular, there is a significant manufacturing challenge in keeping the polymeric substrate 102 flat to ensure a uniform coupling angle for the light 116 that is directed into and reflected out-off the PWG sensor 100. And, there is a significant manufacturing challenge in depositing the waveguide 106 onto the polymeric substrate 102 without damaging the polymeric substrate 102. To address these problems, the PWG sensor 100 can be enhanced by using a flat glass substrate 102 (which is more costly than a polymeric substrate 102) and then forming a polymeric layer onto the glass substrate 102 so the sub-wavelength diffraction grating 104 can be formed into the polymeric layer by embossing, UV curing, or molding. This type of PWG sensor 300 is illustrated in FIG. 3 (PRIOR ART). As shown, the PWG sensor 300 has the following elements:

Flat glass substrate 302.
Polymeric cladding layer 305 (patterned with a sub-wavelength period diffraction grating 304).
Waveguide 306.
Chemically responsive surface chemistry layer 308.
Chemically bound molecules 310 (targets 310) of interest.
Solution 312 containing the substance 314 (analyte 314) to be detected.

The sensitivity of the PWG sensor 300 can be further enhanced if low index polymer layers (not shown) are used instead of the polymeric cladding layer 305. For a more detailed discussion about the structure and the functionality of these types of PWG sensors 300, reference is made to the following documents:

U.S. Patent Application No. 2003/0017580.
PCT Patent Application WO 0235214.
U.S. Patent Application No. 2005/0025421.

The contents of these documents are incorporated by reference herein.

Referring again to FIG. 1, the PWG sensor 100 can be made where the diffraction grating 104 is directly formed into a flat glass substrate 102 by a photolithographic patterning and etching process. This type of PWG sensor 100 is costly but it is desirable because it uses a glass substrate 102 which does not have the flatness problem that is associated with a polymeric substrate 102. In addition, this type of PWG sensor 100 is more durable than the PWG sensor 100 which has the polymeric substrate 102. Because, the waveguide 106 can be deposited onto the glass substrate 102 without the strict restrictions on temperature and ion bombardment that are needed when the waveguide 106 is deposited onto a polymeric substrate 102.

However, the use of a photolithography patterning and etching process to form a smooth and accurately reproduced diffraction grating 104 on the top surface of the glass substrate 102 can be challenging. For example, a PWG sensor 100 has been made where ~0.25 to 0.5 micron linewidths which are required for a subwavelength diffraction grating 104 have been formed in a glass substrate 102 by using a holographic photolithography process (see PCT Patent Application Nos. WO9809156 and WO02082130 and U.S. Pat. No. 6,873,764 B2). Unfortunately, this type of photolithography patterning process can be costly and as such it is not be suitable to manufacture disposable PWG sensors.

Moreover, the etching process which is used to form the diffraction grating 104 within the glass substrate 102 can be a significant challenge itself. For example, silicate glass substrates 102 can be etched by wet etching in a solution containing hydrofluoric acid, or by dry etching in a fluorine containing plasma. However, only simple glass substrates 102 like fused silica may be cleanly etched in this manner. In contrast, most commercial glass substrates 102 have compositions which are complex and contain alkali metals, alkaline earths, aluminum oxide, or transition metal oxides that do not etch well. In particular, the etching of these complex glasses by either a hydrofluoric acid containing solution or a fluorine containing plasma typically produces a rough etch surface, because the fluoride salts of the alkali metals, alkaline earths, aluminum and transition metals are not removed. However, clean features (such as diffraction gratings 104) can be etched for some compositions of glasses using mixed halide gases such as $CCl_2F_2$ when all of the etch products are volatile (see U.S. Pat. No. 6,873,764 B2). And, clean features (such as diffraction gratings 104) may also be plasma etched in some glasses under conditions where sputter etching is utilized (see J. Liu, N. I. Nemchuk, D. G. Ast, and J. G. Couillard, J. Non-Crystalline Solids 342 110 (2004)). Unfortunately, these plasma etching method are not practical for manufacturing large numbers of glass PWG sensors 100.

The aforementioned problems associated with etching clean diffraction gratings 104 in glass substrates 102 can be overcome by depositing a silica layer (which can be easily etched) or a polymer layer onto the glass substrate 102 and then patterning that layer by wet or dry etching. This type of PWG sensor 400 is illustrated in FIG. 4 (PRIOR ART). As shown, the PWG sensor 400 has the following elements:

Flat glass substrate 402.
Discontinuous oxide or polymer layer 405 (which also forms a sub-wavelength period diffraction grating 405).
Waveguide 406.
Chemically responsive surface chemistry layer 408.
Chemically bound molecules 410 (targets 410) of interest.
Solution 412 containing the substance 414 (analyte 414) to be detected.

For a more detailed discussion about the structure and the functionality of PWG sensor 400, reference is made to the following document:

PCT Patent Application WO02082130.

The contents of this document are incorporated by reference herein.

In many of the above PWG sensors, a surface layer (e.g., $SiO_2$) may be deposited on top of the waveguide (e.g., PVD deposited $Nb_2O_5$) to facilitate the formation of a chemoresponsive layer. An exemplary PWG sensor 500 which has this surface layer is illustrated in FIG. 5 (PRIOR ART). As shown, the PWG sensor 500 has the following elements:

Flat glass substrate 502.
Polymer layer 505 (patterned with a sub-wavelength period diffraction grating 504).
Waveguide 506.
Surface layer 507.
Chemically responsive surface chemistry layer 508.
Chemically bound molecules 510 (targets 510) of interest.
Solution 512 containing the substance 514 (analyte 514) to be detected.

For a more detailed discussion about the structure and the functionality of PWG sensor 500, reference is made to the following document:

U.S. Patent Application No. 2004/0043508A1.

The contents of this document are incorporated by reference herein.

In all of the above PWG sensors, a key performance attribute is signal drift. Signal drift occurs when the high index waveguide (and if present the SiO$_2$ surface layer) is porous or cracked which allows the interaction of the solution and the waveguide material. These pores and root cracks are always present in PVD deposited metal oxide waveguides which are deposited over gratings in polymer substrates (see FIG. 1), or deposited over polymer gratings which are on top of glass substrates (see FIG. 3). The pores result from the deposition of the waveguide at a low temperature and under a low ion flux. Under such conditions, adatoms from the vapor arrive at the growth surface and stay where they fall. This produces a columnar grain growth where the packing of adatoms is not optimal, resulting in porosity (see, D. L. Smith, Thin Film Deposition: Principles and Practice, McGraw-Hill (1995) 159–161).

A coating scientist can produce a fully dense oxide coating/waveguide by PVD if they can heat the substrate (typically 250° C. or above) to provide energy for surface diffusion of the adatoms to sites of higher binding energy, and/or if they can use ion bombardment to transfer momentum and pack the adatoms more densely (see D. L. Smith, Thin Film Deposition: Principles and Practice, McGraw-Hill, New York (1995) pp 119–180). However, these methods cannot be used in applications where polymer substrates and/or polymer gratings degrade at temperatures below 200° C. and under ion bombardment. This porosity problem is solved by the present invention.

Moreover, since this PVD coating process is a line of sight process, root cracks are often caused by inadequate step coverage over the grating features. These root cracks may cause signal drift due to infiltration of water during assays. A FIB image which is shown in FIG. 6 (PRIOR ART) illustrates two root cracks 602 that are in the waveguide layer 506 of the prior art PWG sensor 500. As can be seen, this PWG sensor 500 has a UV curable polymer grating 504 formed in a UV curable polymer 505 which is located on a glass substrate 502. FIG. 7 (PRIOR ART) has several plots which illustrate the signal drift (grating resonance vs. time) for 96 PWG sensors 500 (shown in FIGS. 5–6) that are located in a 96 well microplate which contains an aqueous solution. This root problem is solved by the present invention.

An engineering solution to cancel out the effects of signal drift caused by porosity and root cracks in PWG sensors 500 (for example) would be to reference the signal from within one half of each PWG sensor 500 to the other half, or from one PWG sensor 500 to other PWG sensors 500 that are incorporated in the wells of a microplate. For example, in the former solution part of each PWG sensor 500 may be covered or its surface chemistry altered to prevent binding of the target molecules. Then, these PWG sensors 500 would be interrogated. Alternatively, in the later solution a buffer solution can be added to all wells of a microplate, and the biological molecules only to some of the wells in the microplate. Then, the PWG sensors 500 in these wells would be interrogated. However, measurements of differential signal drift may only be used if each PWG sensor 500 in the microplate exhibits a similar signal drift when exposed to the same solutions. Unfortunately, as the plots in FIG. 8 (PRIOR ART) indicate, this is not the case for PWG sensors 500. These plots illustrate the intra-well referenced signal drift (grating resonance vs. time) for 96 PWG sensors 500 located in a 96 well microplate. Accordingly, there is a need to overcome the problematical signal drift that is associated with PWG sensors. This need and other needs are addressed by the present invention.

BRIEF DESCRIPTION OF THE INVENTION

The present invention relates to a PWG sensor which exhibits a lower signal drift and an enhanced sensitivity due to the use of a fully dense silicon rich silicon nitride surface layer. In the preferred embodiment, the silicon rich silicon nitride surface layer has a composition which includes Si and N, and optionally H, Ge and/or O, where a Si/N atomic ratio is greater than 0.75. In addition, the silicon rich silicon nitride surface layer has a refractive index that is greater than 2.45 and less than 3.2 at a wavelength of operation. The present invention also includes a method for manufacturing the PWG sensor with acceptable costs and high yields by utilizing well known semiconductor processes and tools.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 9A:
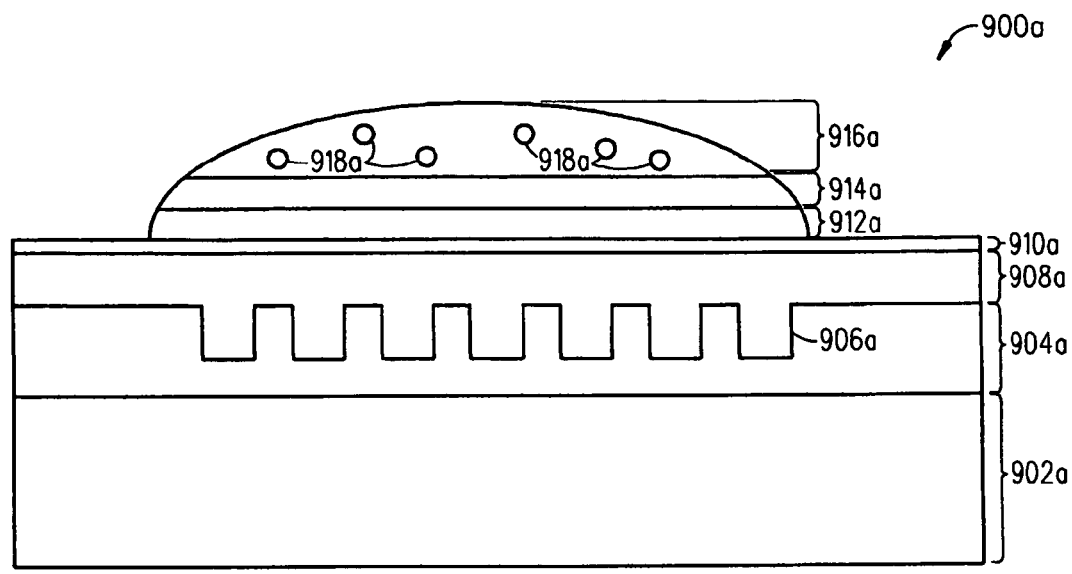
FIGS. 9A and 9B are diagrams of two different embodiments of a PWG sensor in accordance with the present invention.
Figure 9B:
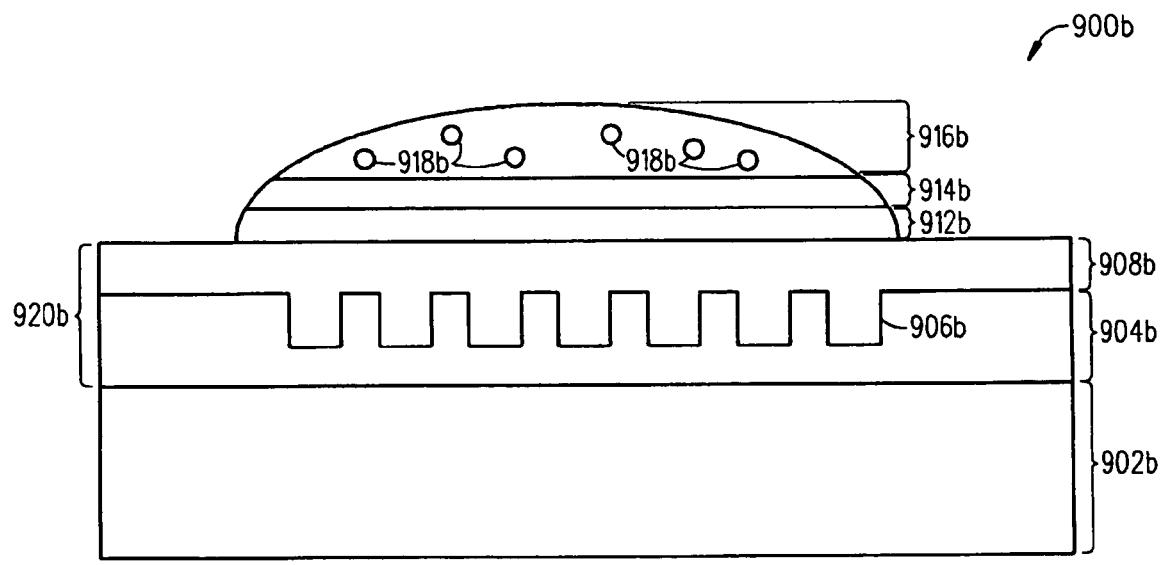

Referring to FIGS. 9A and 9B, there are two block diagrams which illustrate two PWG sensors 900a and 900b configured in accordance with the present invention. As shown in FIG. 9A, the first embodiment of the PWG sensor 900a has the following elements:

Substrate 902a (e.g., glass substrate 902a, polymer substrate 902a).
Low index cladding 904a* (e.g., polymer cladding 904a) that is patterned with a sub-wavelength period diffraction grating 906a).
Monomode waveguide 908a** (e.g., $Nb_2O_5$ waveguide 908a).
Silicon rich silicon nitride surface layer 910a.
Chemically responsive surface chemistry layer 912a.
Chemically bound molecules 914a (targets 914a) of interest.
Solution 916a containing the substance 918a (analyte 918a) to be detected.

As shown in FIG. 9B, the second embodiment of the PWG sensor 900b has the following elements:

Substrate 902b (e.g., glass substrate 902b, polymer substrate 902b).
Low index cladding 904b* (e.g., polymer cladding 904b) that is patterned with a sub-wavelength period diffraction grating 906b).
Silicon rich silicon nitride monomode waveguide 908b.
Chemically responsive surface chemistry layer 912b.
Chemically bound molecules 914b (targets 914b) of interest.
Solution 916b containing the substance 918b (analyte 918b) to be detected.

* It should be noted that the cladding layer 904a and 904b is optional. If it is not used, then the subwavelength period diffraction grating 906a and 906b would be formed in the substrate 902a and 902b (or the waveguide 908a and 908b).

** It should be further noted that the waveguide 908a can be deposited by using one of the following: a solgel technique; a spin on glass technique; a CVD technique (including a PECVD technique, a LPCVD technique, a SACVD technique, or an APCVD technique); or a PVD technique (including a sputtering technique, an e-beam evaporation technique, and an evaporation technique).

In the first embodiment, the PWG sensor 900a has a monomode waveguide 908a that is covered by the silicon rich silicon nitride surface layer 910a (which is preferably 2–10 nm thick). And, in the second embodiment, the PWG sensor 900b has a monomode waveguide 908b that is made from silicon rich silicon nitride (which is preferably greater than 70 nm). In each embodiment, the preferred silicon rich silicon nitride ($SiN_x$) has a composition which includes Si and N, and optionally H, Ge and/or O, where a Si/N atomic ratio is greater than 0.75. In addition, the silicon rich silicon nitride has a refractive index that is greater than 2.45 and less than 3.2 at a wavelength of operation. Although the second embodiment of the PWG sensor 900b is discussed in more detail below, it should be appreciated that the same advantages associated with using the silicon rich silicon nitride material in PWG sensor 900b also applies to the first embodiment of the PWG sensor 900a.

In the present invention, the $SiN_x$ waveguide 908b (or the silicon rich silicon nitride surface layer 910a) is deposited by a step coverage process sufficient to prevent (or at least substantially prevent) problematical root cracks and/or pores from being formed in the grating structure 920b (the area associated with the cladding 904b (if any), the diffraction grating 906b and the waveguide 908b). For a vapor deposited $SiN_x$ coating, this requires deposition at an elevated temperature and/or with ion bombardment. And, this type of deposition process requires a thermally robust substrate 902b and grating structure 920b which are not easily damaged by ion bombardment. Silicate glass is an economical substrate 902b that meets these requirements. For example, precision flat glass such as Corning code 7059, 1737 or 2000 could be used as the substrate 902b.

A preferred grating structure 920b which can meet these requirements is described next. A preferred grating structure 920b is one that has a smooth and accurately reproduced diffraction grating 906b with a sub-micron pitch which is formed into the top surface of the substrate 902b (this is not the grating structure 920b shown in FIG. 9B). However, since it is difficult to cleanly wet etch or dry etch in fluorine plasma most commercial precision flat glass, a thin cladding layer 904b of a more easily etched material (within which the diffraction grating 906b can be etched) such as a doped or undoped silicon oxide (e.g., silica) can be deposited over the glass substrate 902b (this is the grating structure 920b shown in FIG. 9B). For instance, the silica cladding layer 904b can be deposited by using a PECVD, a SACVD or a LPCVD technique any of which are well known in the semiconductor industry. If the silica cladding 904b is doped with fluorine, germanium, boron, phosphorous and/or nitrogen, then it is possible to adjust the refractive index, thermal stress, and etch rate of the silica cladding 904b. In addition, the silica cladding 904b if desired may be annealed to help stabilize the refractive index and hydrolytic stability.

After depositing the cladding 904b, the diffraction grating 906b is etched therein. In the preferred embodiment, the diffraction grating 906b can be etched within the cladding 904b by using a photolithography process during which a resist is deposited over the cladding 904b and then the resist is patterned such that the cladding 904b can be etched through exposed areas in the resist to form the diffraction grating 906b. For instance, a diffraction grating 906b with quarter micron linewidths could be economically formed within the cladding 904b by using: (1) a 248 nm projection lithography (stepper) and reactive ion etch (or wet etch); or (2) a 4× or higher magnification i-line stepper and reactive ion etch (or wet etch).

Figure 6:
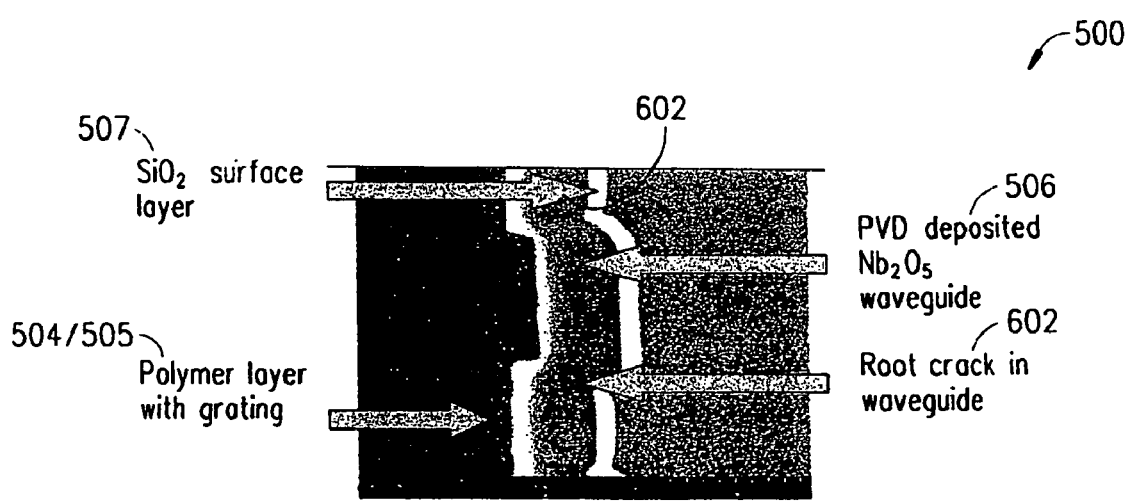
Figure 7:
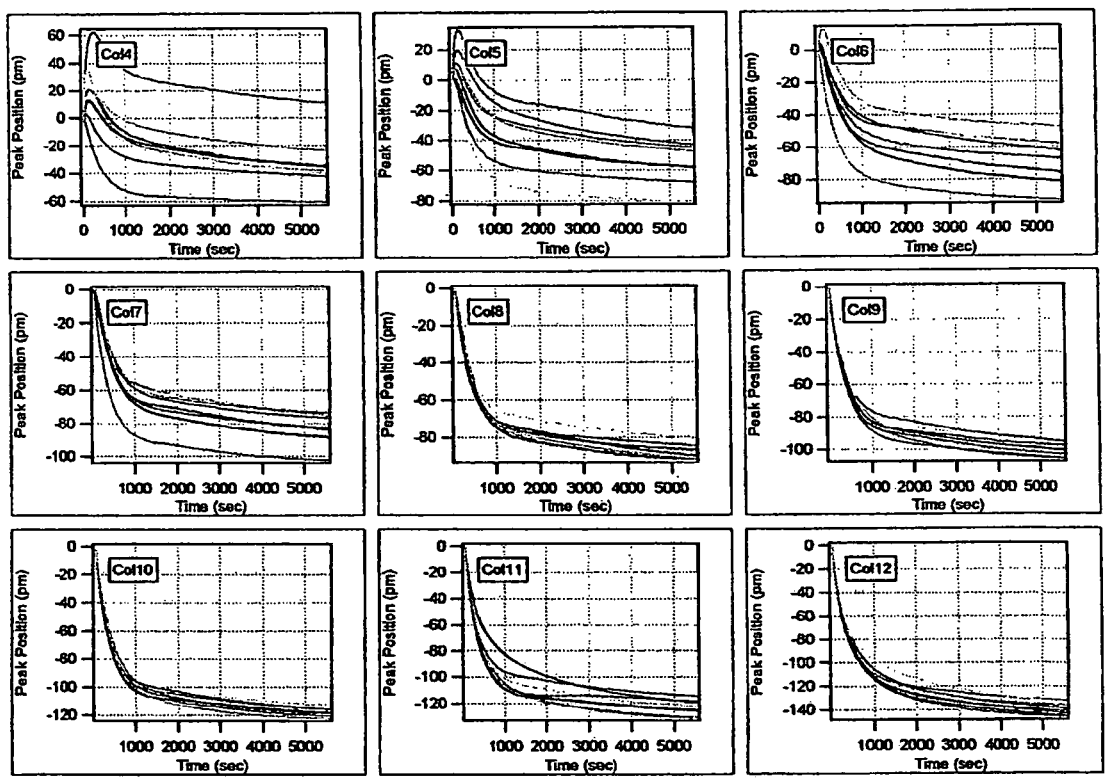
Figure 8:
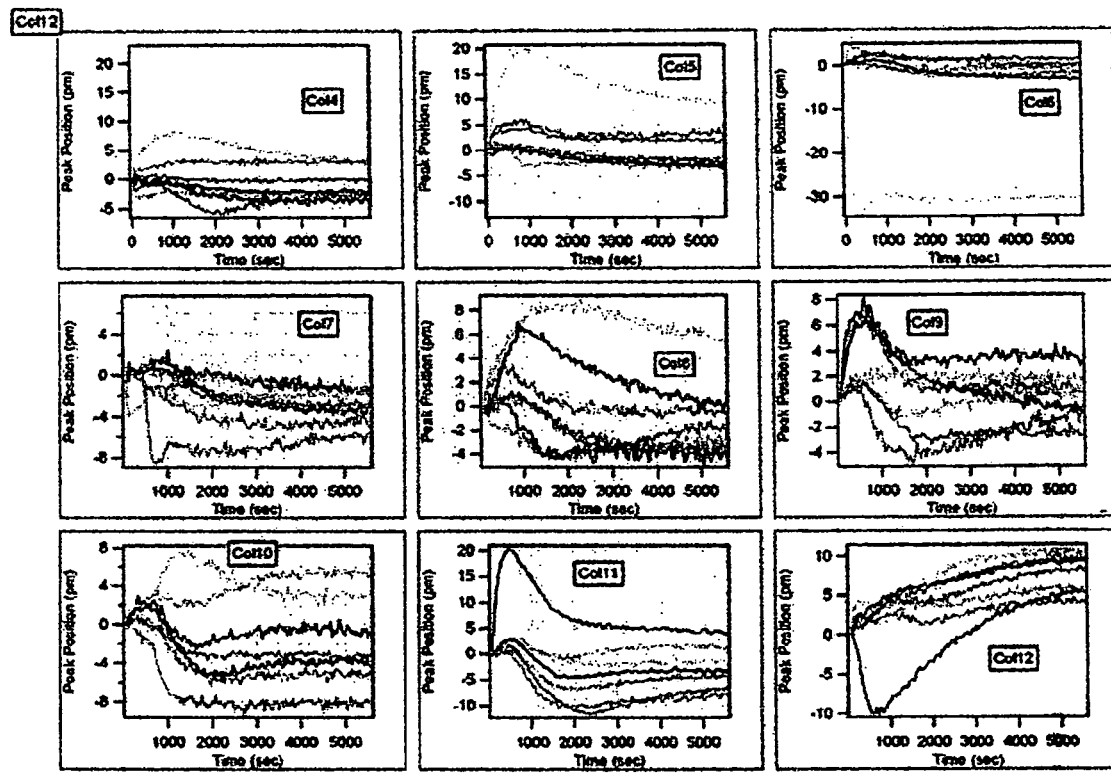
Figure 10:
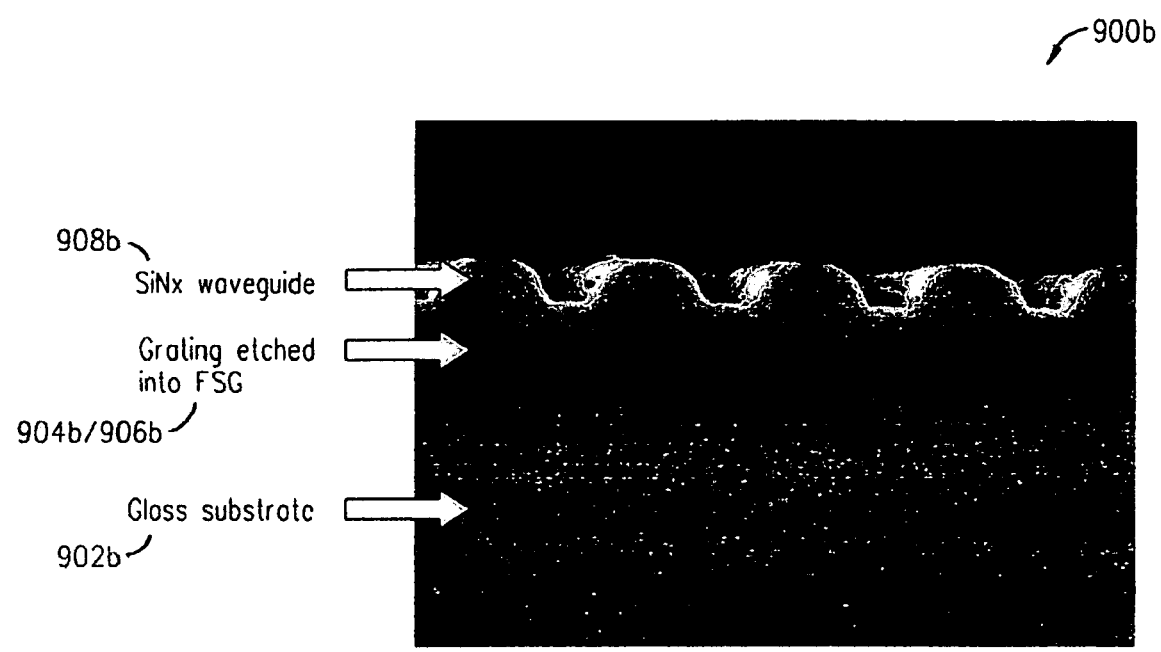
FIG. 10 is a SEM cross-sectional image of a PWG sensor that is configured like the PWG sensor shown in FIG. 9B.

At this point, a fully dense silicon rich silicon nitride waveguide 908b has been deposited over the diffraction grating 906b by a process which minimizes the formation of root cracks and/or voids. The preferred deposition process is CVD because it produces films with conformal coverage. As can be seen in FIG. 10, this conformal coverage leads to a fully dense waveguide 908b which has no cracks or voids (compare to FIG. 6). FIG. 10 illustrates a SEM cross-sectional image of a 140 nm thick silicon rich silicon nitride waveguide 908b which is deposited over a 55 nm deep diffraction grating 906b which is etched in a 200 nm thick FSG cladding layer 904b that is deposited on Corning code 1737 glass substrate 902b.

Figure 11:
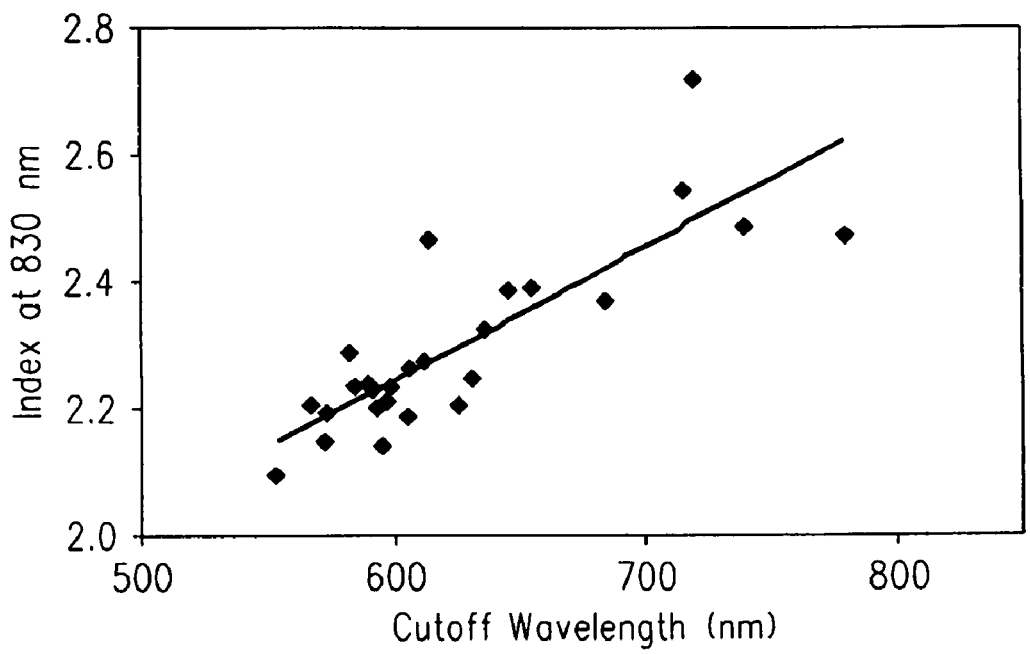
FIG. 11 is a plot illustrating the refractive index at 830 nm vs. cutoff wavelength for silicon rich silicon nitride which is used in the PWG sensors shown in FIGS. 9A and 9B.

The refractive index of the silicon rich silicon nitride can be adjusted from 1.9 to 3.2 at 830 nm by changing the concentration of silicon, nitrogen, and hydrogen (e.g., see W. R. Knolle, Thin Solid Films 168 (1989) 122). The raising of the refractive index causes the adsorption edge to move from near 300 nm to over 800 nm as the index rises from 1.9 to 3.2. Of particular interest for higher sensitivity PWG sensors 900a and 900b is the use of silicon rich silicon nitride compositions where the Si/N ratio exceeds the stoichiometric ratio of 3/4 (and preferably >2.0). These silicon rich silicon nitrides when compared to previously used silicon nitrides have a higher refractive index, a lower stress, an absorption edge in the visible range, and more hydrogen bound to Si. And, the silicon rich silicon nitride composition can be set to maximize refractive index and minimize absorption in the waveguide 908b at the wavelength of interest. FIG. 11 is a graph that shows the refractive index of silicon rich silicon nitride vs the cutoff wavelength where k>1E−4 for films deposited from silane and ammonia in a typical parallel plate PECVD system over a range of reactant flows, reactor pressure, RF power, and electrode configurations. From this graph it can be seen that sufficiently low optical absorption can be achieved with a silicon rich silicon nitride that has a refractive index of over 2.75 at 830 nm. This feature permits the use of silicon rich silicon nitride as a high index waveguide 908b (or surface layer 910a).

Figure 12:
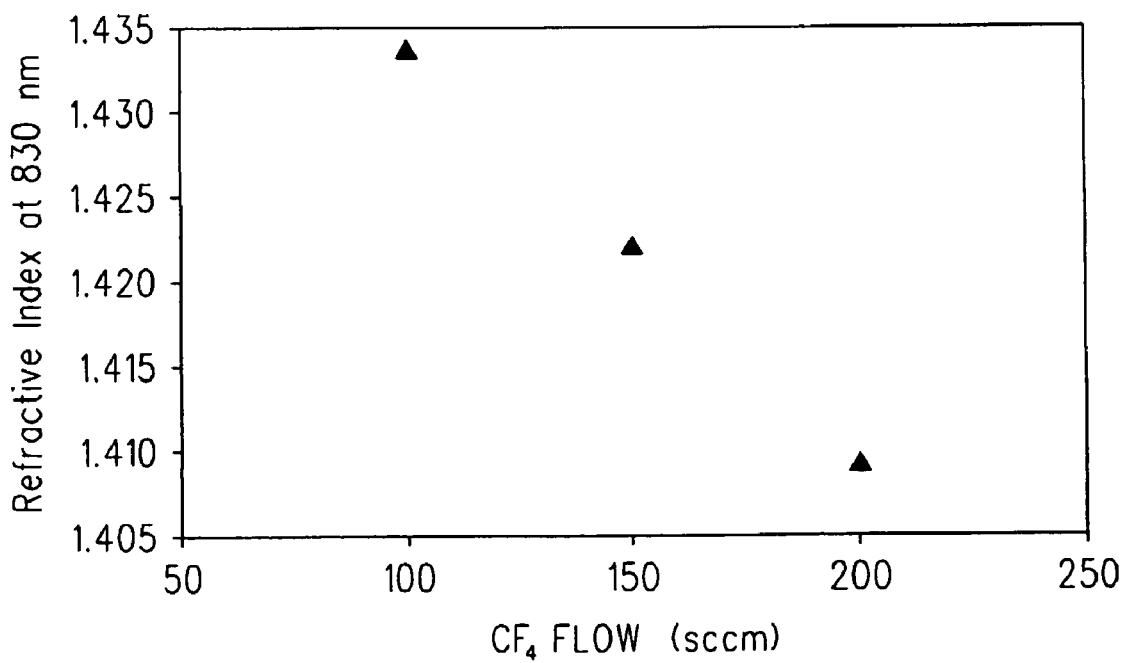
FIG. 12 is a plot illustrating the refractive index at 830 nm vs. CF$_4$ flow for PECVD deposited FSG cladding which can be used in the PWG sensors shown in FIGS. 9A and 9B.

To further increase the index contrast between the waveguide 908b and the cladding layer 904b/substrate 902b, one can lower the refractive index of the cladding layer 904b. Fluorine is the most effective dopant for lowering the refractive index of a silica cladding layer 904b. However, the moisture sensitivity of the silica cladding layer 904b increases with the fluorine content which puts a limit on the fluorine content. Ab initio configuration interaction calculations have predicted the lower limit of FSG stability against moisture at 10–12 at % F (see H. Yang and G. Lucosky, J. Vac. Sci. Tech. A16(3) 1525). A practical limit of ~9 at % F, corresponding to a refractive index of 1.4150 at 830 nm was chosen for the PWG sensor 900b shown in FIG. 10. The FSG films 904b of this composition were deposited from controlled additions of a fluorine containing gas such as $CF_4$, $C_2F_6$, or $C_4F_8$ to a PECVD silicon dioxide process which also used silane and nitrous oxide. FIG. 12 is a plot which shows the refractive index at 830 nm vs. $CF_4$ flow for PECVD deposition of an exemplary FSG film 904b.

Figure 1:
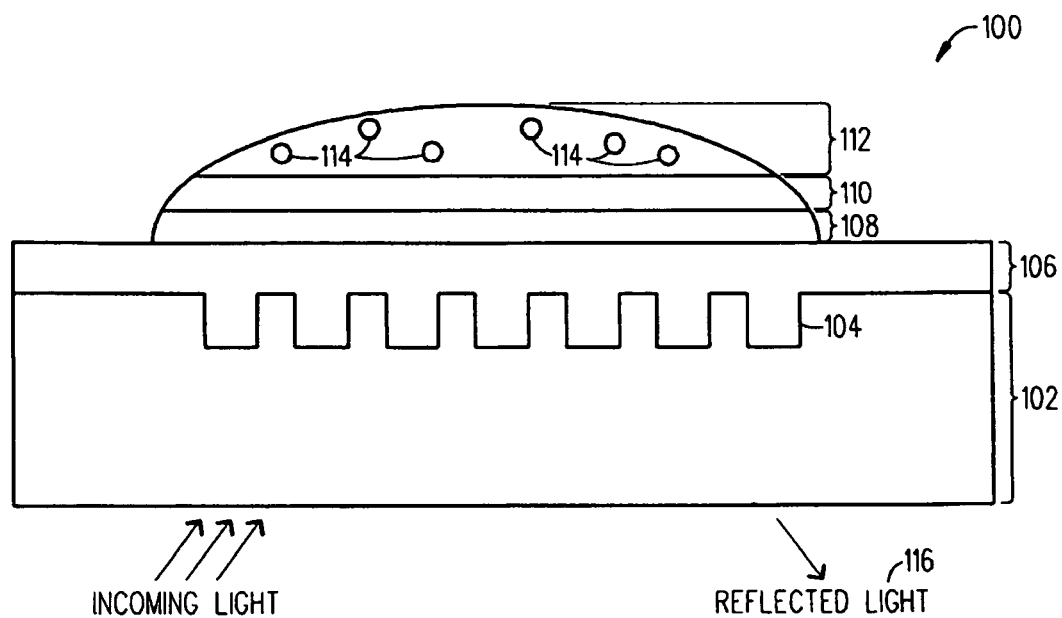
FIG. 1 (PRIOR ART) is a cross-sectional diagram that shows the basic elements of a PWG sensor which is disclosed in U.S. Pat. No. 4,815,843.
Figure 2:
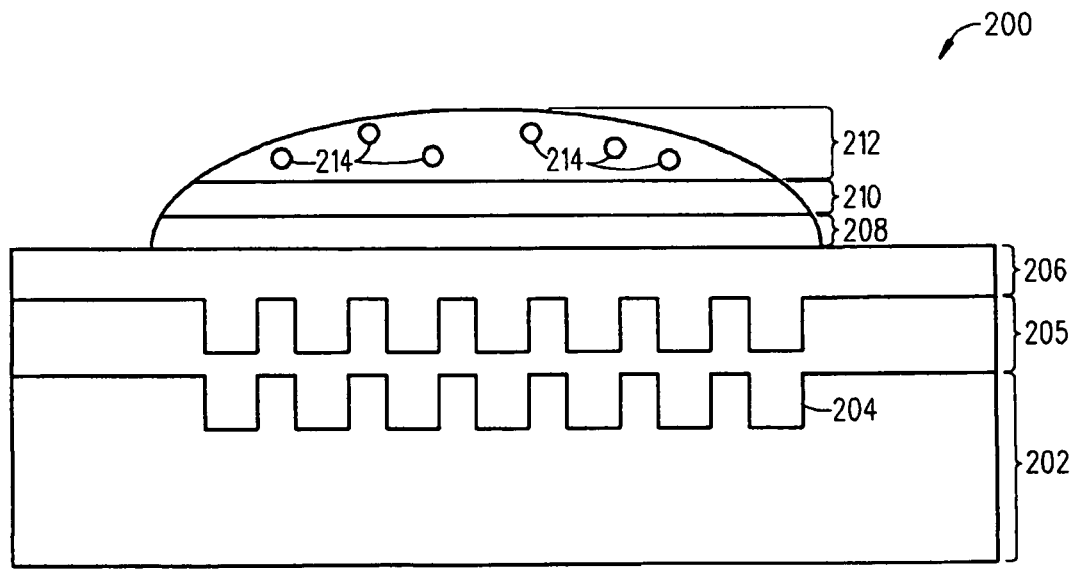
FIG. 2 (PRIOR ART) is a cross-sectional diagram that shows the basic elements of a PWG sensor which is disclosed in U.S. Pat. No. 5,369,722.
Figure 3:
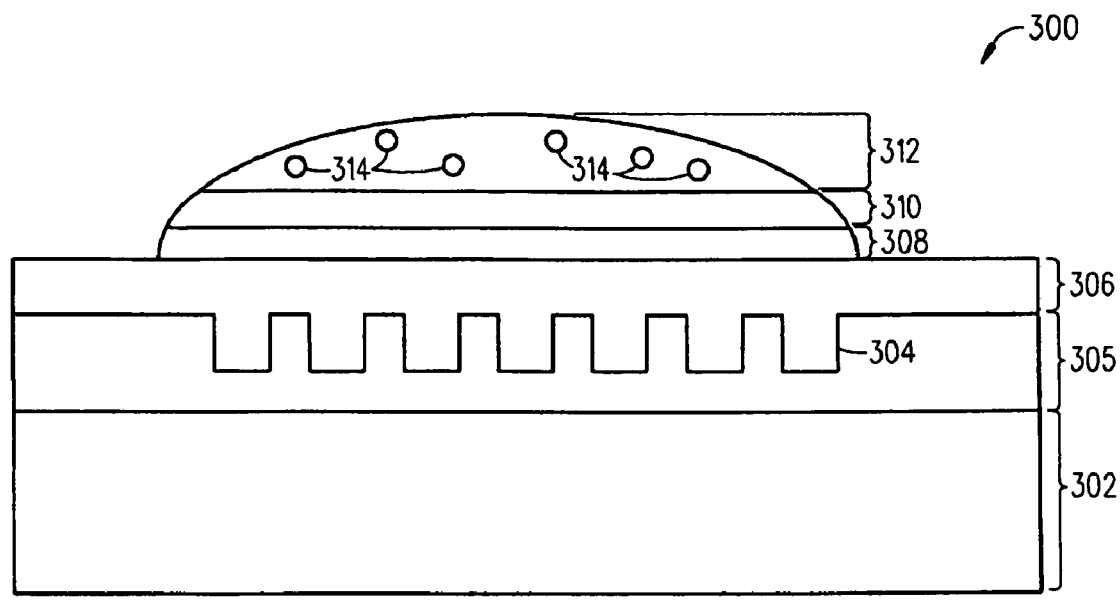
FIG. 3 (PRIOR ART) is a cross-sectional diagram that shows the basic elements of a PWG sensor which is disclosed in PCT Patent Application WO 0235214.
Figure 4:
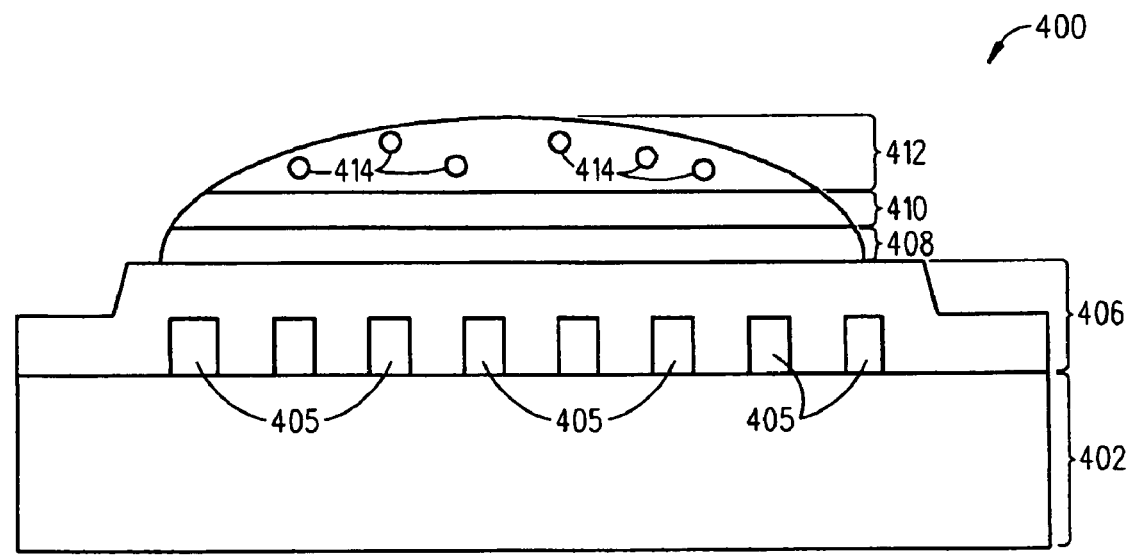
FIG. 4 (PRIOR ART) is a cross-sectional diagram that shows the basic elements of a PWG sensor which is disclosed in PCT Patent Application WO02082130.
Figure 5:
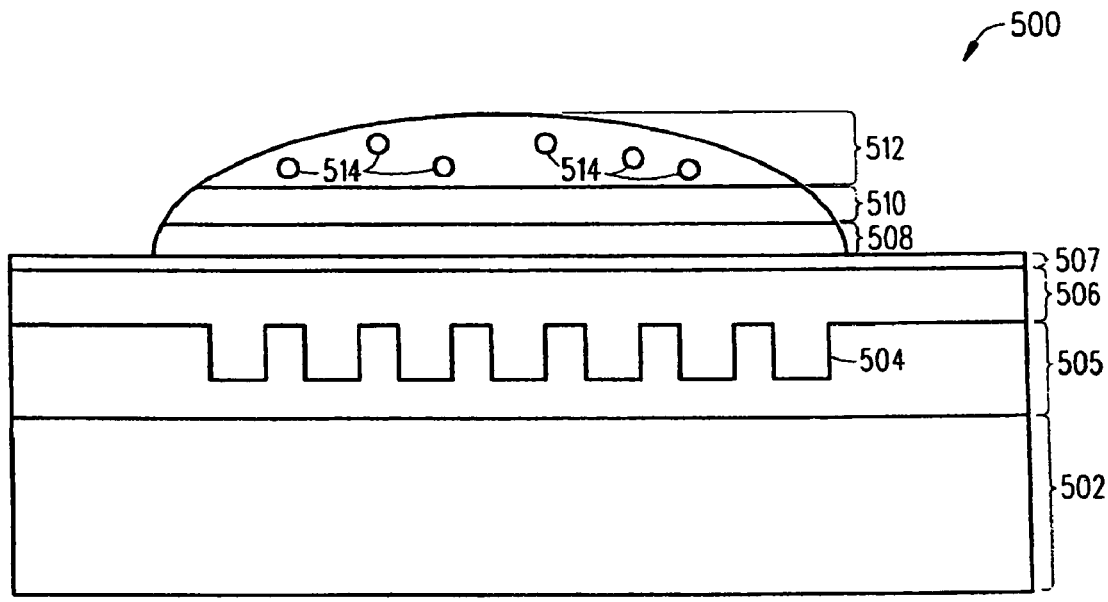
FIGS. 5–8 (PRIOR ART) are diagrams used to help describe the structure and functionality of a PWG sensor which is disclosed in U.S. Patent Application No. 2004/0043508A1.
Figure 13A:
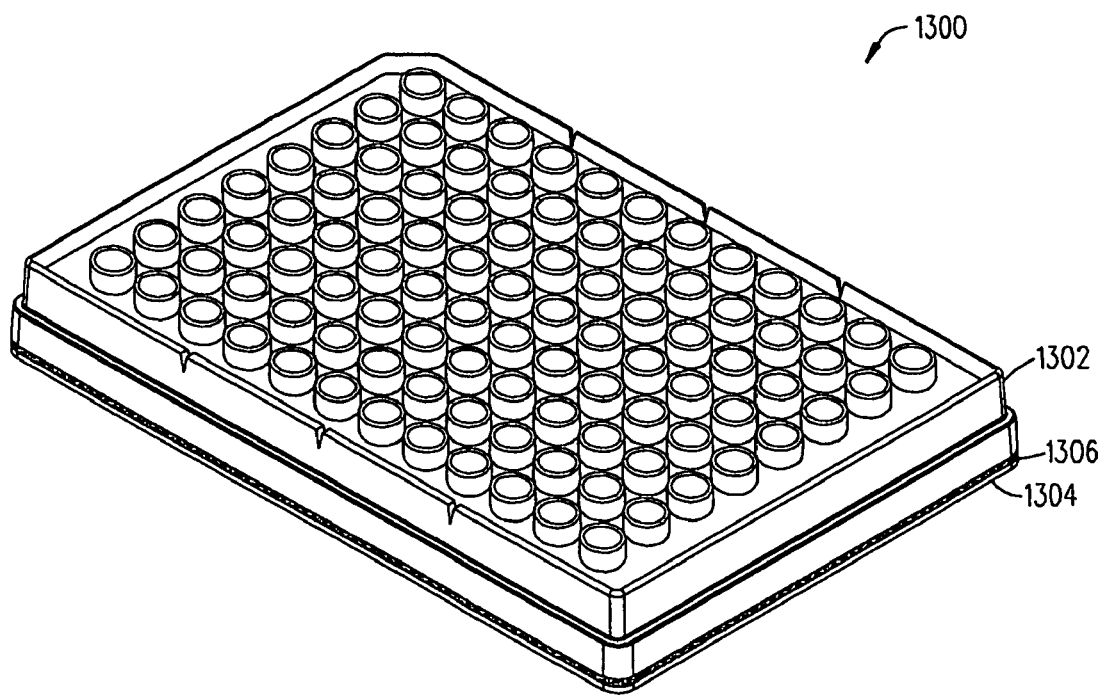
FIGS. 13A and 13B are two diagrams of an exemplary 96 well microplate which can incorporate 96 PWG sensors like the PWG sensors shown in FIGS. 9A and 9B.
Figure 13B:
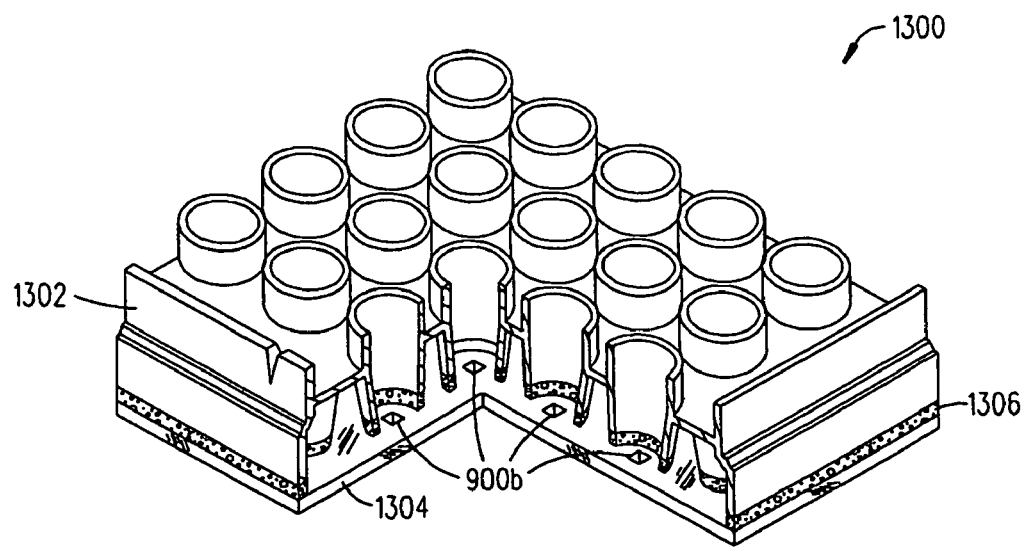

Example A: An experiment was conducted so the signal drift and theoretical sensitivity of the PWG sensor 900b (shown in FIG. 9B) could be compared to the prior art PWG sensor 500 (shown in FIGS. 5–6). In order to conduct this experiment, a 96 well microplate 1300 similar to the one shown in FIGS. 13A and 13B was manufactured which had 96 PWG sensors 900b that where fabricated by PECVD depositing a 200 nm fluorinated silica glass (FSG) cladding layer 904b which had a refractive index of 1.41 at 830 nm onto the glass substrate 902 (Corning Code 1737 glass). A diffraction grating 906b pattern was then formed in the FSG cladding layer 904b by exposing a photoresist with a deep UV stepper, and a 65 nm deep diffraction grating 906b was etched into the FSG cladding layer 904b by using a RIE process and fluorocarbon gas $CHF_3$. A ~120 nm thick Si-rich silicon nitride monomode waveguide 908b with a refractive index of 2.75 at 830 nm was then PECVD deposited over the diffraction grating 906b/FSG cladding layer 904b, and an optional 5 nm thick silica surface layer was deposited over the waveguide 908b by PECVD (see FIG. 9B). The 96 well microplate 1300 was then formed by bonding a polymer holey well plate 1302 to the inorganic planar waveguide grating 1304 with a UV curable adhesive 1306.

Figure 14:
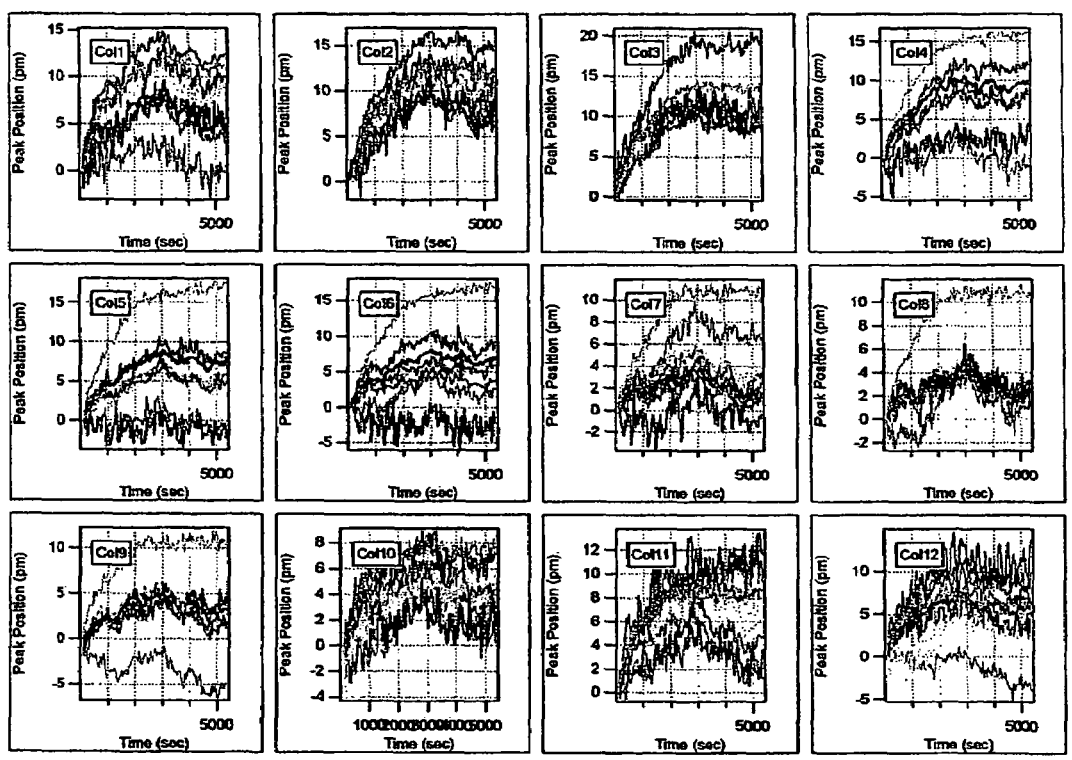
FIG. 14 is a series of plots that illustrate the signal drift (grating resonance vs. time) for 96 PWG sensors (see FIG. 9B) which are exposed to an acqueous solution in a 96 well microplate.
Figure 15:
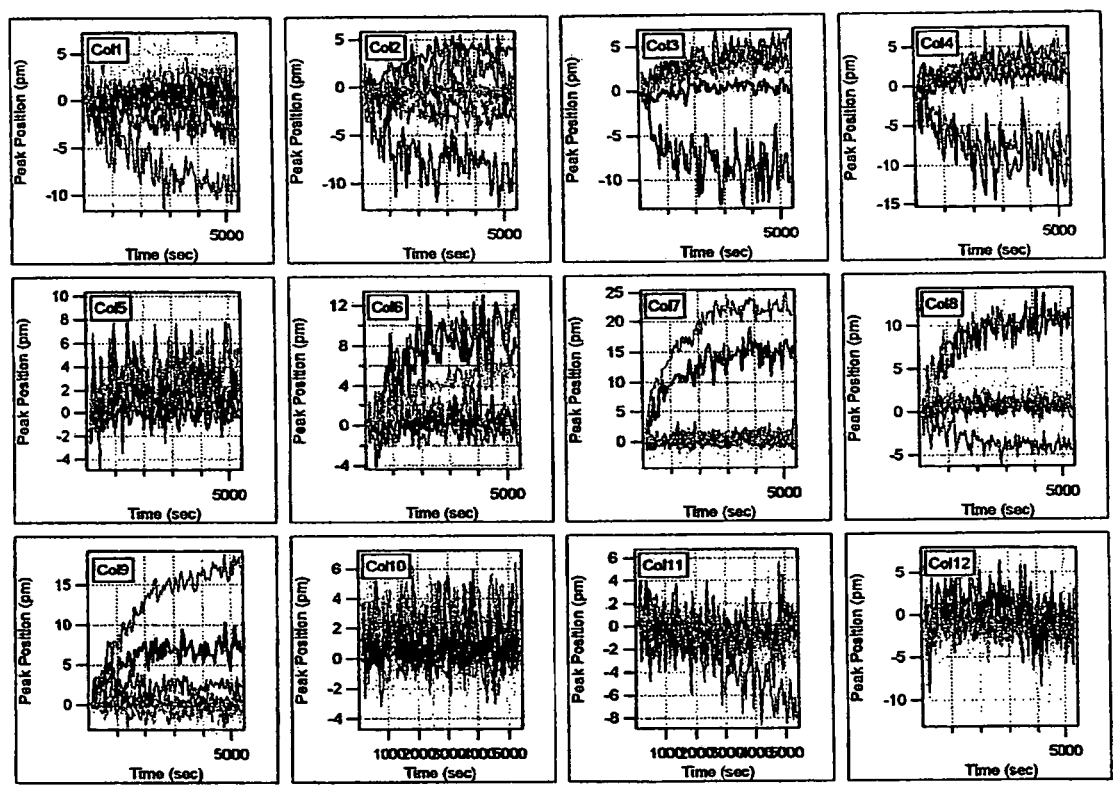
FIG. 15 is a series of plots that illustrate the intra-well referenced signal drift (grating resonance vs. time) for 96 PWG sensors (see FIG. 9B) which are exposed to an aqueous solution in a 96 well microplate.

The signal drift of several PWG sensors 900b which were in contact with de-ionized water is shown in the plots illustrated in FIGS. 14 and 15. FIG. 14 illustrates plots of signal drift (grating resonance vs. time) for 96 PWG sensors 900b which were exposed to an acqueous solution in microplate 1300. As can be seen, these plots show that the inorganic PWG sensors 900b exhibit a drift of only 0.01 to 0.05 pm/min after 30 minutes of exposure to the aqueous solution. The higher initial drift is believed to happen while the PWG sensors 900b and aqueous solution attained thermal equilibrium. And, FIG. 15 illustrates plots of intra-well referenced signal drift (grating resonance vs. time) for 96 PWG sensors 900b which where exposed to an aqueous solution in microplate 1300. As can be seen, these plots show the intra-well referenced drift between the PWG sensors 900b as being only 0.005 to 0.015 pm/min after 30 minutes of exposure to the aqueous solution. TABLE 1 compares the drift rates of the PWG sensor 900b to the prior art PWG sensor 500 (see FIGS. 5–8).

TABLE 1

| Observed numbers for most of the wells | PWG sensor 500 (see FIGS. 5–8) | PWG sensor 900b (see FIGS. 9B and 14–15) |
| --- | --- | --- |
| Total Absolute Drift (0 to 30 min) | −60 pm to −120 pm | 10 to 15 pm |
| Absolute Drift Rate (30 to 90 min) | 0.150 pm/min to 0.25 pm/min | 0.01 pm/min to 0.05 pm |
| Referenced Drift Rate (30 to 90 mm) | 0.01 pm/min to 0.03 pm/min | 0.005 pm/min to 0.015 pm/min |

As can be seen, the inorganic PWG sensor 900b had a lower and more uniform signal drift than prior art PWG sensor 500. This is due to the conformal coverage of the waveguide 908b and the exceptional uniformity of the grating structure 920b. And, since all the PWG sensors 900b in the wells drift in a similar manner, one can reference between the different PWG sensors 900b to cancel out the effect of signal drift. As can be seen, this greatly increased the sensitivity of the response of the PWG sensor 900B.

In this example, the sensitivity of the inorganic PWG sensor 900b was determined by measuring the shift in the resonant wavelength as the index of refraction changed when liquid was added to the microplate 1300. The refractive index of the solution was changed by adding glycerol to water. The resonant wavelength was determined for a series of water-glycerol mixtures containing 1–40 vol % glycerol. And, then the sensitivity of each PWG sensor 900b was obtained by performing a linear fit to the plot of the wavelength shifts vs. refractive index of the water glycerol solution. In this experiment, the average slope of the microfabricated PWG sensor 900b was 110 nm/RIU, vs. 80 nm/RIU for the prior art PWG sensor 500. The PWG sensor 500 had a $Nb_2O_5$ waveguide 506, a 2 nm $SiO_2$ surface layer 507, and a UV formed polymer grating 504/505 (see FIGS. 5–6).

Example B: Another experiment was conducted so the assay performance of Fl-biotin interacting with immobilized Streptavidin could be compared by using 384 well microplates which had either inorganic PWG sensors 900b or prior art PWG sensors 500 incorporated therein.

The inorganic PWG sensor 900b array was fabricated by depositing onto a glass substrate 902b a 200 nm FSG cladding layer 904b which had a refractive index of 1.41 at 830 nm by PECVD. Then, grating patterns 906b were formed in the FSG cladding layer 904b by exposing a photoresist with a deep UV stepper, and 45 nm deep diffraction gratings 906b were etched into the FSG cladding layer 904b by using a RIE process and fluorocarbon gas $CHF_3$. Then, a ~148 nm thick Si-rich silicon nitride monomode waveguide 908b with a refractive index of 2.5 at 830 nm was deposited by PECVD over the diffraction gratings 904b. The prior art PWG sensor 500 array was fabricated by forming diffraction gratings 504 in a UV cured polymer layer 505 located on a glass substrate 502. Then, a $Nb_2O_5$ waveguide 506 was PVD deposited over the UV cured polymer layer 505. And, a 2 nm thick SiO$_2$ surface layer 507 was deposited over the Nb$_2$O$_5$ waveguide 506. Both types of PWG sensor arrays were then bonded to 384 holey well plates with a UV curable adhesive, and subsequently coated with aminoproyl silsesquioxane (APS) and poly(ethylene-alt-maleic anhydride) (EMA) to form the chemoresponsive layer 508/912b which was used to bind the Streptavidin 510/914b.

TABLE 2 compares the Fl-biotin to Streptavidin assay performance between microfabricated 384 well microplates which contained the PWG sensors 900b and 384 well microplates which contained the prior art PWG sensors 500.

assay signal after the binding with Streptavidin is constant for the new inorganic 384 well microplate.

Referring back to TABLE 2, the average signal drift that is observed prior to addition of the Fl-biotin is shown in the two right columns. As can be seen, the signal drift is significantly lower for the new 384 well inorganic microplates than the prior art 384 well microplates. And, the difference in the signal drift in different rows is lower as seen by results for rows A, C, and E vs. B, D, and F. This difference is important to determine if referencing between wells (PWG sensors) could be utilized to reduce the signal drift. Also, it is important to note that the low drift rates

TABLE 2

| Plate Number | Plate Type | AVE (pm) | STDEV | % CV | Soak Time (ACE) | Approximate Drift (pm/min) (rows ACE) | Approximate Drift (pm/min) (rows BDF) |
|---|---|---|---|---|---|---|---|
| 1 | Prior Art | 23.40 | 1.14 | 4.87 | 5 Hours | −0.60 | −0.20 |
| 2 | New | 30.02 | 1.50 | 4.98 | 1 Hour | +0.05 | +0.05 |
| 3 | New | 34.52 | 1.55 | 4.48 | 5.5 Hours | +0.15 | +0.10 |
| 4 | Prior Art (FIG. 16) | 23.33 | 1.52 | 6.54 | 4.5 Hours | −0.35 | −0.25 |
| 5 | New (FIG. 17) | 29.09 | 1.61 | 5.52 | 50 Minutes | +0.15 | 0.00 |
| 6 | New | 30.67 | 1.03 | 3.35 | 4.75 Hours | +0.075 | +0.075 |

In this experiment, three rows of wells were measured at once, with rows A, C, E measured first, and B, D, and F next. Upon addition of the Fl-biotin the grating resonance was observed to shift by an average of ~30 pm for the inorganic 384 well microplates (which contained PWG sensors 900b) when compared to ~23.5 pm for the 384 well microplates (which contained the prior art PWG sensors 500). The differences in the assay results between the inorganic 384 well microplates (which contained PWG sensors 900b) and the 384 well microplates (which contained the prior art PWG sensors 500) can be seen in the assay curves shown in FIGS. 16 and 17.

Figure 16:
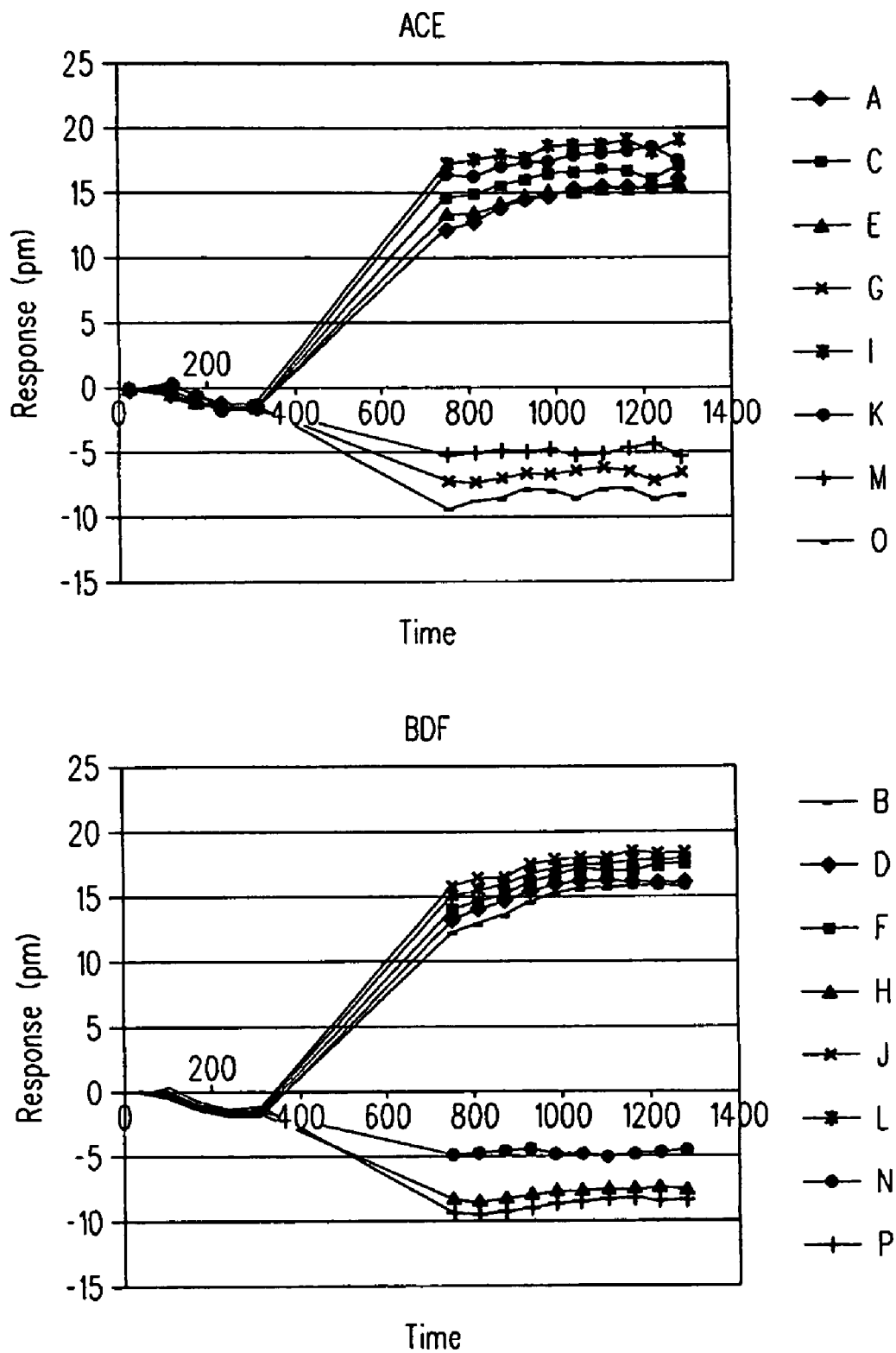
FIG. 16 (PRIOR ART) illustrates two graphs which indicate the results of an experiment that was conducted to test known PWG sensors that are similar to the one shown in FIG. 6.
Figure 17:
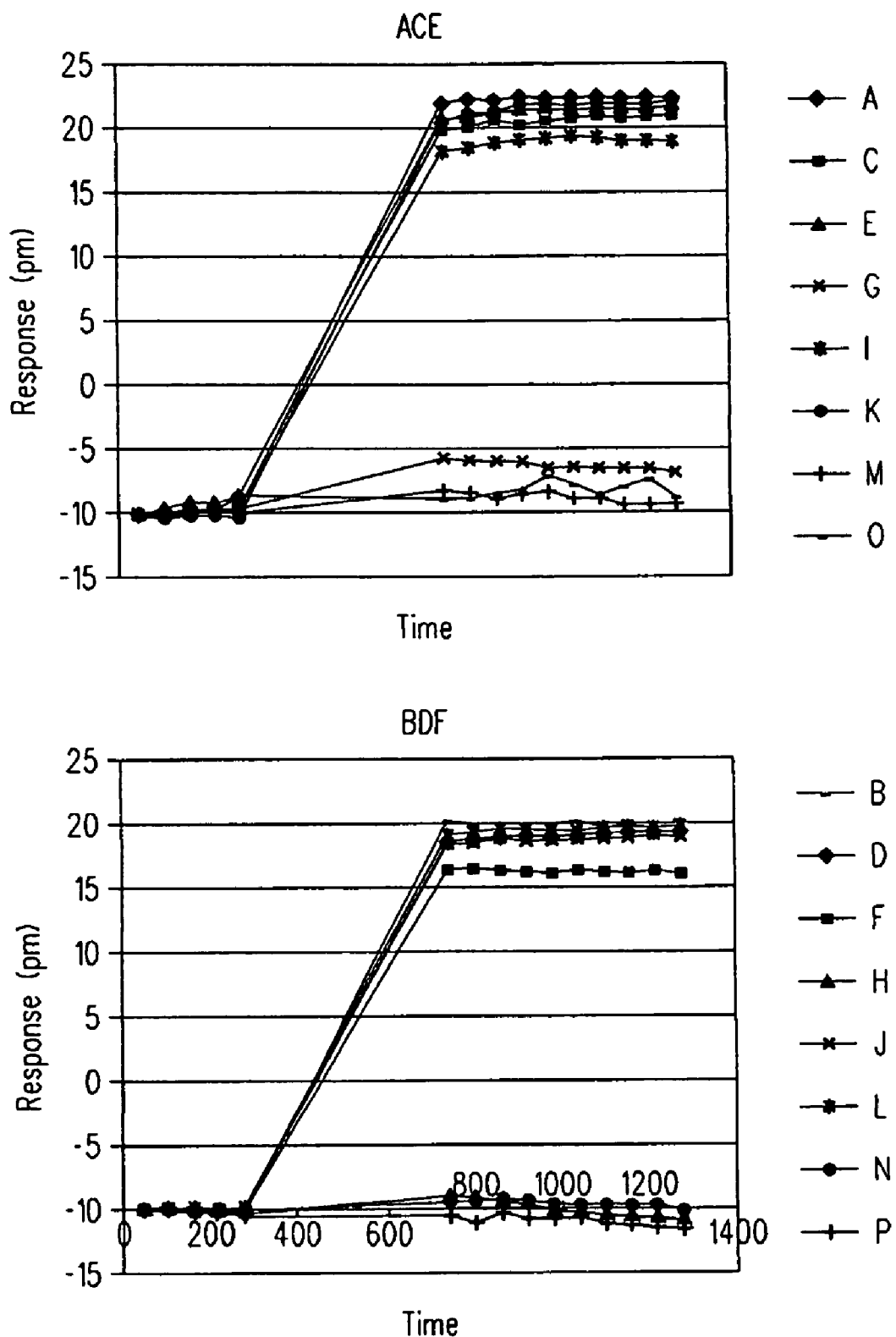
FIG. 17 illustrates two graphs which indicates the results of an experiment that was conducted to test new PWG sensors that are similar to the one shown in FIG. 9B.

FIG. 16 (PRIOR ART) illustrates two graphs of a Fl-biotin on Streptavidin assay signal from column 12 rows ACE (top graph) and BDF (bottom graph) showing both the assay signal and the signal drift using the 384 well microplate which contained the prior art PWG sensors 500. While, FIG. 17 illustrates two graphs of a Fl-biotin on Streptavidin assay signal from column 12 rows ACE (top graph) and BDF (bottom graph) showing both the assay signal and the signal drift using the inorganic 384 well microplate which contained the new PWG sensors 900b. In comparing the plots in FIGS. 16 and 17, a significant negative drift can seen with the prior art 384 well microplate prior to introducing the Fl-biotin, and the assay signal is seen to rise and roll off with time after the addition of the Fl-biotin. In contrast, the signal drift before the introduction of Fl-biotin is smaller, and the where achieved after soaking the new inorganic microplates in a buffer for ~1 hr vs. the 4.5 hrs plus required before the drift of the prior art microplates would stabilize.

Example C: This experiment was conducted to examine if the origin of the higher assay signal for the inorganic PWG sensors 900a and 900b was due to the higher index contrast of the waveguide structure, or to the surface interaction between the waveguide structure, the surface chemistry layer 912a and 912b, and the solution containing the molecules 914a and 914b of interest. Eight microplates of either inorganic PWG sensors 900a or 900b as described above with respect to FIGS. 9A and 9B but with different waveguides and surface layers where tested and the Fl-biotin to Streptavidin assay results compared. The waveguide materials compared were the Nb$_2$O$_5$ waveguides (PWG sensor 900a) as was typically used in prior art example PWG sensor 500, and silicon rich silicon nitride (PWG sensor 900b). The surface layers compared were SiO$_2$ surface as was typically used in prior art example PWG sensor 500, and silicon rich silicon nitride surface layers described in PWG sensors 900a and 900b. Both silicon-rich silicon nitride and SiO$_2$ surface layers were deposited by both PECVD and PVD (sputtering). All eight microplates were coated with aminoproyl silsesquioxane (APS) and poly (ethylene-alt-maleic anhydride) (EMA). The results of this experiment are shown in TABLE 3.

TABLE 3

| Sample | Waveguide | Waveguide Index | Waveguide Thickness (nm) | Cover | Cover Thickness (nm) | Assay Signal (pm) | CV (%) |
|---|---|---|---|---|---|---|---|
| 1+ | SiN$_x$ | 2.75 | 121 | SiO$_2$ PECVD | 2 | 22.4 | 7.1 |
| 2+ | SiN$_x$ | 2.75 | 121 | | | 31.3 | 5.2 |
| 3+ | SiN$_x$ | 2.50 | 148 | | | 30.5 | 7.8 |

TABLE 3-continued

| Sample | Waveguide | Waveguide Index | Waveguide Thickness (nm) | Cover | Cover Thickness (nm) | Assay Signal (pm) | CV (%) |
|---|---|---|---|---|---|---|---|
| 4 | $Nb_2O_5$ | 2.30 | 168 | $SiO_2$ PVD | 7 | 23.5 | 8.3 |
| 5+ | $SiN_x$ | 2.50 | 148 | $SiO_2$ PVD | 7 | 22.0 | 8.3 |
| 6 | $Nb_2O_5$ | 2.30 | 168 | $SiO_2$ PECVD | 7 | 23.5 | 9.6 |
| 7 | $Nb_2O_5$ | 2.30 | 165 | $SiN_x$ PECVD | 5 | 27.61 | 7.6 |
| 8 | $Nb_2O_5$ | 2.30 | 165 | $SiN_x$ PVD | 9 | 30.61 | 8.2 |

+Samples 1, 2, 3 and 5 are similar to PWG sensor 900b except that they have a silica surface layer.

A clear distinction can be seen between the microplates with a $SiO_2$ surface layer and those with a silicon-rich nitride surface. In particular, the assay signal on microplates with $SiO_2$ surface layers averaged 22.9 pm, vs. 30.0 for the microplates with silicon-rich silicon nitride surfaces. No significant difference was observed between PVD and PECVD deposited $SiO_2$, PVD and PECVD deposited silicon-rich silicon nitride, and between 2.75 index and 2.5 index silicon-rich silicon nitride. These results indicate that the sensitivity increase is due to the silicon-rich silicon nitride surface and this effect dominates the effects of the waveguide structure.

From the foregoing, it should be appreciated by those skilled in the art that the silicon rich silicon nitride surface layer or waveguide can also be used in any of the aforementioned prior art PWG sensors (see FIGS. 1–5). As such, the present invention can be applied to PWG sensors that have a polymer substrate, a glass substrate with doped oxide cladding layer, or a glass substrate with a polymer grating layer. In addition, the present invention can be applied to PWG sensors that do not have the cladding layer.

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A planar waveguide grating (PWG) sensor comprising a silicon rich silicon nitride surface layer which has at least one of the following: (1) a composition which includes at least Si and N where a Si/N atomic ratio is greater than 0.75; and (2) a refractive index that is greater than 2.45 and less than 3.2 at a wavelength of operation.

2. The PWG sensor of claim 1, wherein said silicon rich silicon nitride surface layer has a composition that further includes H, Ge, and/or O.

3. The PWG sensor of claim 1, wherein said silicon rich silicon nitride surface layer has a thickness that is greater than 70 nm which is sufficient to form a waveguide.

4. The PWG sensor of claim 3, wherein said waveguide is formed by said silicon rich silicon nitride surface layer which is deposited by using one of the following:
   a PECVD technique;
   a LPCVD technique;
   a SACVD technique;
   an APCVD technique, or
   a PVD technique which includes:
      a sputtering technique;
      an e-beam evaporation technique; and
      an evaporation technique.

5. The PWG sensor of claim 1, further comprising a waveguide layer which has a thickness sufficient to form a monomode waveguide and a refractive index that is greater than 2.0 at the wavelength of operation.

6. The PWG sensor of claim 5, wherein said silicon rich nitride surface layer is deposited over said waveguide layer by using one of the following:
   a sol-gel technique;
   a spin on glass technique;
   a CVD technique which includes:
      a PECVD technique;
      a LPCVD technique;
      a SACVD technique; or
      an APCVD technique; or
   a PVD technique which includes:
      a sputtering technique;
      an e-beam evaporation technique; and
      an evaporation technique.

7. The PWG sensor of claim 1, further comprising a <1 micron thick oxide cladding layer which has a composition of Si, O, F, and optionally H, Ge, B, P and/or N, and has a refractive index that is less than 1.45 at the wavelength of operation.

8. The PWG sensor of claim 7, wherein said <1 micron thick oxide cladding layer is formed by using one of the following CVD techniques:
   a PECVD technique;
   a LPCVD technique;
   a SACVD technique;
   an APCVD technique, or
   a PVD technique which includes:
      a sputtering technique;
      an e-beam evaporation technique; and
      an evaporation technique.

9. The PWG sensor of claim 7, further comprising a surface grating structure which is formed in said oxide cladding layer.

10. The PWG sensor of claim 9, wherein said surface grating structure is formed by a photolithography process which uses an i-line or 248 nm stepper and reactive ion etch.

11. The PWG sensor of claim 9, wherein said surface grating structure is formed by a photolithography process uses an i-line or 248 nm stepper and wet etch.

12. The PWG sensor of claim 1, further comprising a substrate.

13. A microplate comprising:
a frame including a plurality of wells formed therein, each well incorporating a planar waveguide grating (PWG) sensor that includes:
a silicon rich silicon nitride surface layer which has at least one of the following: (1) a composition which includes at least Si and N where a Si/N atomic ratio is greater than 0.75; and (2) a refractive index that is greater than 2.45 and less than 3.2 at a wavelength of operation.

14. The microplate of claim 13, wherein said silicon rich silicon nitride surface layer has a composition that further includes H, Ge, and/or O.

15. The microplate of claim 13, wherein said silicon rich silicon nitride surface layer has a thickness that is greater than 70 nm which is sufficient to form a monomode waveguide.

16. The microplate of claim 13, wherein said silicon rich nitride surface layer is deposited over a waveguide layer which has a thickness sufficient to form a monomode waveguide and a refractive index that is greater than 2.0 at the wavelength of operation.

17. The microplate of claim 13, wherein said PWG sensor further comprising a cladding layer which has a composition of Si, O, F, and optionally H, Ge, B, P and/or N, and has a refractive index that is less than 1.45 at the wavelength of operation.

18. The microplate of claim 17, wherein said PWG sensor further comprising a surface grating structure which is formed in said cladding layer.

19. The microplate of claim 17, wherein said PWG sensor further comprising a substrate.

20. A method for producing a planar waveguide grating (PWG) sensor, said method comprising the steps of:
providing a substrate;
depositing, onto said substrate, a cladding layer;
forming, in said cladding layer, a surface grating structure;
depositing, onto said cladding layer and said surface grating structure, a waveguide layer which has a thickness sufficient to form a monomode waveguide; and
forming, onto said waveguide layer, a silicon rich silicon nitride surface layer which has at least one of the following: (1) a composition which includes at least Si and N where a Si/N atomic ratio is greater than 0.75; and (2) a refractive index that is greater than 2.45 and less than 3.2 at a wavelength of operation.

21. The method of claim 20, wherein said step of forming said silicon rich silicon nitride surface layer is performed by using one of the following:
a PECVD technique;
a LPCVD technique;
a SACVD technique;
an APCVD technique, or
a PVD technique which includes:
a sputtering technique;
an e-beam evaporation technique; and
an evaporation technique.

22. A method for producing a PWG sensor, said method comprising the steps of:
providing a substrate;
depositing, onto said substrate, a cladding layer;
forming, in said cladding layer, a surface grating structure;
depositing, onto said cladding layer and said surface grating structure, a silicon rich silicon nitride surface layer which has a thickness sufficient to form a monomode waveguide and which also has at least one of the following: (1) a composition which includes at least Si and N where a Si/N atomic ratio is greater than 0.75; and (2) a refractive index that is greater than 2.45 and less than 3.2 at a wavelength of operation.

23. The method of claim 22, wherein said waveguide is formed by said silicon rich silicon nitride surface layer which is deposited by using one of the following:
a PECVD technique;
a LPCVD technique;
a SACVD technique;
an APCVD technique, or
a PVD technique which includes:
a sputtering technique;
an e-beam evaporation technique; and
an evaporation technique.

* * * * *